United States Patent
Prasanna Kumar et al.

(10) Patent No.: US 10,623,113 B2
(45) Date of Patent: Apr. 14, 2020

(54) METHOD AND APPARATUS FOR START-OF-PACKET DETECTION IN DIGITAL COMMUNICATION SYSTEMS

(71) Applicant: KONINKLIJKE PHILIPS N.V., Eindhoven (NL)

(72) Inventors: Jagruth Prasanna Kumar, Eindhoven (NL); Anteneh Alemu Abbo, Eindhoven (NL); Gerardus Johannus Jacobus Maria Arnoldussen, Eindhoven (NL); Sotir Filipov Ouzounov, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/082,994

(22) PCT Filed: Feb. 24, 2017

(86) PCT No.: PCT/EP2017/054263
§ 371 (c)(1),
(2) Date: Sep. 7, 2018

(87) PCT Pub. No.: WO2017/153181
PCT Pub. Date: Sep. 14, 2017

(65) Prior Publication Data
US 2019/0103924 A1 Apr. 4, 2019

(30) Foreign Application Priority Data
Mar. 9, 2016 (EP) .................................. 16159293

(51) Int. Cl.
H04B 13/00 (2006.01)
H04L 7/04 (2006.01)
(Continued)

(52) U.S. Cl.
CPC ......... *H04B 13/005* (2013.01); *H04L 1/0083* (2013.01); *H04L 7/042* (2013.01);
(Continued)

(58) Field of Classification Search
CPC ... H04B 13/005; H04L 7/042; H04L 27/2656; A61B 5/0024; A61B 5/0028
See application file for complete search history.

(56) References Cited

U.S. PATENT DOCUMENTS

| 7,151,759 | B1 | 12/2006 | Ryan |
| 7,415,661 | B2 | 8/2008 | Keaney |

(Continued)

FOREIGN PATENT DOCUMENTS

| CA | 2215380 A1 | 9/1996 |
| EP | 0549247 A1 | 6/1993 |
| JP | S6133040 A | 2/1986 |

OTHER PUBLICATIONS

Kwak et al.; An Overview of IEEE 802.15.6 Standard) Feb. 20, 2011 (Year: 2011).*

(Continued)

*Primary Examiner* — Gary Mui

(57) ABSTRACT

A start of packet detector comprises an input which receives start of packet information. The detector has a first stage which determines if there is a match between a respective subset of received start of packet information with a respective subset of reference start of packet information. The first stage repeats the determining for each of the subsets of received start of packet information and said respective subset of reference start of packet information. An output will provide a start of packet detected output which is dependent on the determining of the first stage.

12 Claims, 8 Drawing Sheets

(51) Int. Cl.
*H04L 1/00* (2006.01)
*H04L 27/26* (2006.01)
*A61B 5/00* (2006.01)

(52) U.S. Cl.
CPC ........ *H04L 27/2656* (2013.01); *A61B 5/0024* (2013.01); *A61B 5/0028* (2013.01)

(56) References Cited

U.S. PATENT DOCUMENTS

| | | | |
|---|---|---|---|
| 7,480,234 | B1 | 1/2009 | Hart |
| 7,809,020 | B2 | 10/2010 | Douglas |
| 8,139,582 | B2 | 3/2012 | Park |
| 2004/0005023 | A1 | 1/2004 | Ham |
| 2006/0209784 | A1* | 9/2006 | Cheng Gang ........... H03M 9/00 370/350 |
| 2007/0160174 | A1 | 7/2007 | Yang |
| 2010/0272156 | A1* | 10/2010 | Park ..................... H04B 13/005 375/142 |
| 2010/0287402 | A1* | 11/2010 | Kim ........................ H04J 3/067 713/400 |
| 2011/0085505 | A1* | 4/2011 | Kang ................... A61B 5/0024 370/329 |
| 2011/0200150 | A1* | 8/2011 | Fazzi ................... H04B 13/005 375/343 |
| 2012/0027149 | A1 | 2/2012 | Mutchnik |
| 2012/0089370 | A1* | 4/2012 | Chebbo ................ A61B 5/0002 702/188 |
| 2013/0016762 | A1* | 1/2013 | Tanaka .................. H04W 28/06 375/219 |
| 2013/0243111 | A1* | 9/2013 | Lee ....................... H04L 25/022 375/285 |
| 2015/0009014 | A1* | 1/2015 | Mo ..................... G06K 7/10366 340/10.1 |
| 2015/0043696 | A1* | 2/2015 | Nair ........................ H04B 1/30 375/364 |
| 2016/0292426 | A1* | 10/2016 | Gibart ..................... G06F 21/85 |
| 2017/0111123 | A1* | 4/2017 | Ouzounov ........... H04B 13/005 |
| 2017/0149599 | A1* | 5/2017 | Kang ..................... H04B 1/707 |
| 2017/0180059 | A1* | 6/2017 | Kim ........................ H04W 4/70 |
| 2017/0257175 | A1 | 9/2017 | Ouzounov |

OTHER PUBLICATIONS

Lande, T.S. et al., "Running Cross-Correlation Using Bitstream Processing", Electronics Letters, vol. 43, No. 22, pp. 1181-1182, Oct. 2007.

Fazzi, A. et al., "A 2.75mW Wideband Correlation-Based Transceiver for Body-Coupled Communication", Proceedings of the IEEE International Solid-State Circuits Conference 2009, ISSCC 2009, Feb. 8-12, 2009, San Francisco, California.

Creusere, C.D. et al., "Bitstream-Based Correlation Detector for Multi-View Distributed Video Coding Applications", 2008 IEEE International Conference on Acoustics, Speech and Signal Processing, IEEE 2008, pp. 1001-1004.

Constandinou, Dr. T.G. et al., "Energy Efficient Bitstream Cross-Correlation", Downloaded from the Internet Aug. 29, 2018 http://www3.imperial.ac.uk/people/t.constandinou/research/bitstream.

* cited by examiner

METHOD AND APPARATUS FOR START-OF-PACKET DETECTION IN DIGITAL COMMUNICATION SYSTEMS

TECHNICAL FIELD

Some embodiments relate to a method and apparatus for start-of-packet (SOP) detection for use in particular but not exclusively in body coupled devices.

BACKGROUND

Body-coupled communications (BCC) or body-based communication has been proposed as a as a basis for body area networks (BANs) as standardized by the 802.15.6 Task Group of the Institute of Electrical and Electronics Engineers (IEEE). BCC allows exchange of information between a plurality of devices which are at or in close proximity of a body of a human or an animal. This can be achieved by capacitive or galvanic coupling of low-energy electric fields onto the body surface.

In body-coupled communication (BCC) systems information is transmitted from a transmission device to a receiver device via signals across the user's body. Body-coupled communication may utilize an electric field to transmit information.

Body-coupled communication (BCC) uses the human body as communication channel. It enables wireless communication over a human body between devices that are in contact with that human body. Signals are conveyed over the body instead of through the air. As such, the communication is confined to an area close to the body. Therefore, communication is possible between devices situated on, connected to, or placed close to the body.

Reference is now made to FIG. 6 which shows a known start of packet (SOP) detector 203. A data packet 300 is received which has a field contain start of packet data. The start of packet detector has a reference SOP buffer 601 which has reference SOP data, an SOP buffer 602 which receives the SOP from the received data packet, and comparison circuitry 603. The comparison circuitry will determine if there is a match between the reference SOP and the received SOP and provide an appropriate output 604. The comparison circuitry may use a parallel multi-bit correlation (PMBC) approach to detect the SOP data in the received message.

US2012/027149 describes a synchronisation detector where matches are checked between a continuously fed shift register and a single reference word.

EP0549247 describes a synchronisation detector for a D2 MAC system where the result of comparisons for odd and even frame synchronisation sequences are OR'd together.

JPS6133040 describes and analogue synchronisation detector.

CA2215380 describes a coding systems and apparatus which has synchronisation detector.

This technique works well in a number of situations. Where the signal-to-noise ratio is low, the detection can become less reliable and a typical solution is to make the SOP longer. However, with increased lengths of SOP, the increasing complexity and power consumption of the SOP detector may be disadvantageous in certain applications.

SUMMARY

According to an aspect, there is provided a start of packet detector comprising: an input configured to receive input data comprising start of packet information; a first stage configured to determine if there is a match between a respective subset of received start of packet information with a respective subset of reference start of packet information, said first stage being configured to repeat said determining for each of subsets of received start of packet information and said respective subset of reference start of packet information, wherein a value of a counter is changed if there is a match between a respective subset of received start of packet information with a respective subset of reference start of packet informati; and an output configured to provide a start of packet detected output, said start of packet detected output being dependent on a comparison of said determining of said first stage a value of said counter with a threshold.

Where larger lengths of SOPs are used, some embodiments of the present invention allow a more compact and/or power efficient SOP detector to be provided. This is because the same circuitry is used to look at subsets of the start of packet information. This means that the amount of circuitry required can be reduced. This may also reduce power consumption.

A counter may be configured to control which respective subset of reference start of packet information is used by said first stage. This may ensure that each subset of reference start of packet information is used in the correct order. It should be appreciated that in other embodiments, different logic may be used.

A value of the counter may be changed if there is a match between a respective subset of received start of packet information with a respective subset of reference start of packet information. The counter may be incremented or decremented. In this way, when a give value of the counter is achieved, it can be determined that the whole of the SOP has been checked.

The first stage may be configured to use a threshold to determine if there is a match, said threshold be configurable for each subset. This allows for the threshold to be varied, for example in response to noise level.

The first stage may comprise an exclusive OR function configured to perform a respective exclusive OR function between said received start of packet information subset and the respective reference start of packet information subset. The exclusive OR function will advantageously provide one value when the reference and received value are the same and a different value when the reference and received value are different.

The first stage may comprise an adder function configured to add the output of said exclusive OR function and to provide a summed output to a first comparator, said first comparator configured to compare said summed output to a threshold. Advantageously, by summing the output of the exclusive OR function, a value is obtained which will be indicative of the degree of match between the reference and received start of packet information. By comparing this value to a threshold, it can be simply determined if the respective subsets of information are considered to be a match or not.

The first stage may be configured to cause a start of packet detected output to be output by said output if all the subsets of said start of packet information have been determined to match. This may be simple to implement in that if any respective subsets do not match, then it is considered that there is no match.

The start of packet detector may comprise a second comparator for determining if all the subsets of said start of packet have been determined for a match may b and if so to cause a start of packet detected output to be output by said output.

The start of packet detector may comprise a second stage arranged in parallel with said first stage, said second stage configured to compare said respective subset of received start of packet information with an inverse of the respective subset of reference start of packet information and said output is configured to provide a start of packet detected output, said start of packet detected output being dependent on said determining of said first stage or said second stage. This is useful with devices which do have a common electrical ground. The detector may therefore interpret the received message as being the opposite polarity (i.e. the binary 1's may be interpreted as 0's and vice versa). Accordingly, by having the second stage, the SOP detector is able to consider both possible polarities.

The output may be configured to output information indicating if said start of packet detected output is dependent on said determining of said first stage or said second stage. In some embodiments, this may be used for understanding the content of the packet.

According to another aspect, there is provided a body coupled device comprising a start of packet detector as described above. Body coupled device advantageously should be low power devices and may be operated in relatively noisy requirements, requiring longer start of packet information which may be supported by some embodiments.

According to another aspect, there is provided a method of detecting a start of packet comprising: receiving a first subset of received start of packet information; comparing the first subset of received start of packet information with a respective first subset of reference to determine if there is a match; repeating said receiving and comparing steps for subsequent subsets of received start of packet information and respective subsets of reference start of packet information; and providing a start of packet detected output dependent on said comparing steps.

The comparing may comprise using a threshold to determine if there is a match.

The comparing may comprise using a first threshold with said first subset of received start of packet information and a second different threshold with at least one other subset of received start of packet information.

The method may comprise providing a start of packet detected output if all the subsets of said start of packet information have been determined to match.

The method may comprise using a count value to control which respective subset of reference start of packet information is used.

The method may comprise changing the count value if there is a match between a respective subset of received start of packet information with a respective subset of reference start of packet information.

The method may comprise performing an exclusive OR function between said received start of packet information subset and the respective reference start of packet information subset.

The method may comprise performing an add function to add results of said exclusive OR function and to provide a summed output, and comparing the summed output to a threshold.

The method may comprise repeating said method using an inverse of reference start of packet information and the start of packet detected output is dependent on said determining using the reference start of packet information or its inverse.

The method may comprise providing information indicating if said start of packet detected output is dependent on the reference start of packet information or its inverse.

Namely, the present embodiment describes a method of improved start-of-packet (SOP) detection under varying noise conditions.

BRIEF DESCRIPTION OF THE DRAWINGS

Some embodiments will now be described by way of example only and with reference to the accompanying Figures in which.

DETAILED DESCRIPTION

Some embodiments may provide a start of packet detector comprising: an input configured to receive input data comprising start of packet information; a first stage configured to determine if there is a match between a respective subset of received start of packet information with a respective subset of reference start of packet information, the first stage being configured to repeat the determining for each of subsets of received start of packet information and the respective subset of reference start of packet information; and an output configured to provide a start of packet detected output, the start of packet detected output being dependent on the determining of the first stage. Where larger lengths of SOPs are used, some embodiments of the present invention allow a more compact and/or power efficient SOP detector to be provided. This is because the same circuitry is used to look at subsets of the start of packet information. This means that the amount of circuitry required can be reduced. This may also reduce power consumption.

Figure 1:
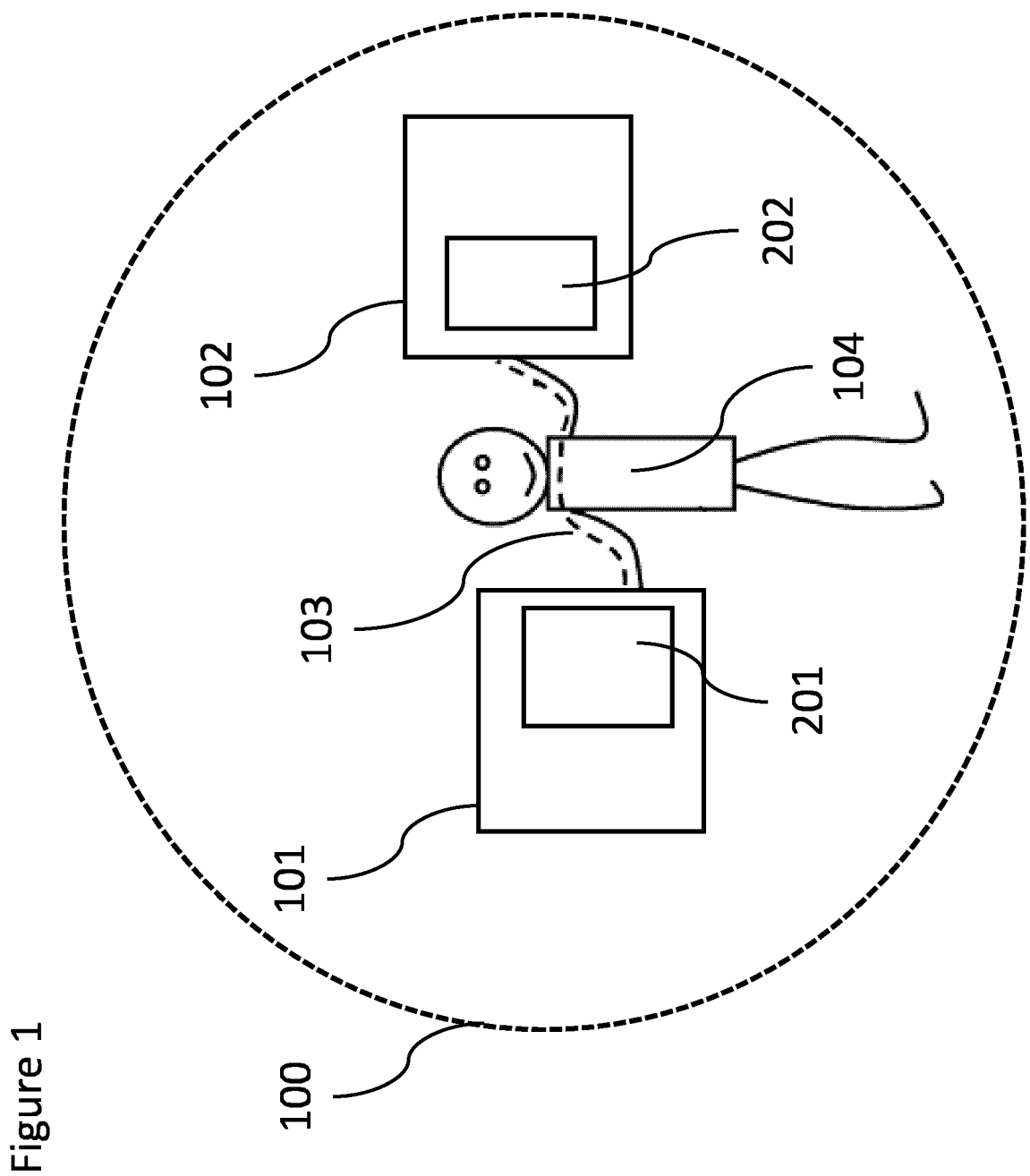
FIG. 1 schematically shows an embodiment of a body-coupled communication BCC system.

Reference is now made to FIG. 1 which shows a wireless body area network (WBAN) 100, comprising a first BCC device 101, and a second BCC device 102. In some embodiments more than two BCC devices are utilized. The first BCC device 101, is able to communicate with a second BCC device 102 via a communication channel 103 in the body of a person 104. For example, the first BCC device 101 contains a transmitter 201, and the second BCC device 102 contains a receiver 202. It should be appreciated that the first BCC device 101 may have both a transmitter and a receiver or just a transmitter. The second BCC device 102, may also have both a transmitter and a receiver or just a receiver.

Figure 2:
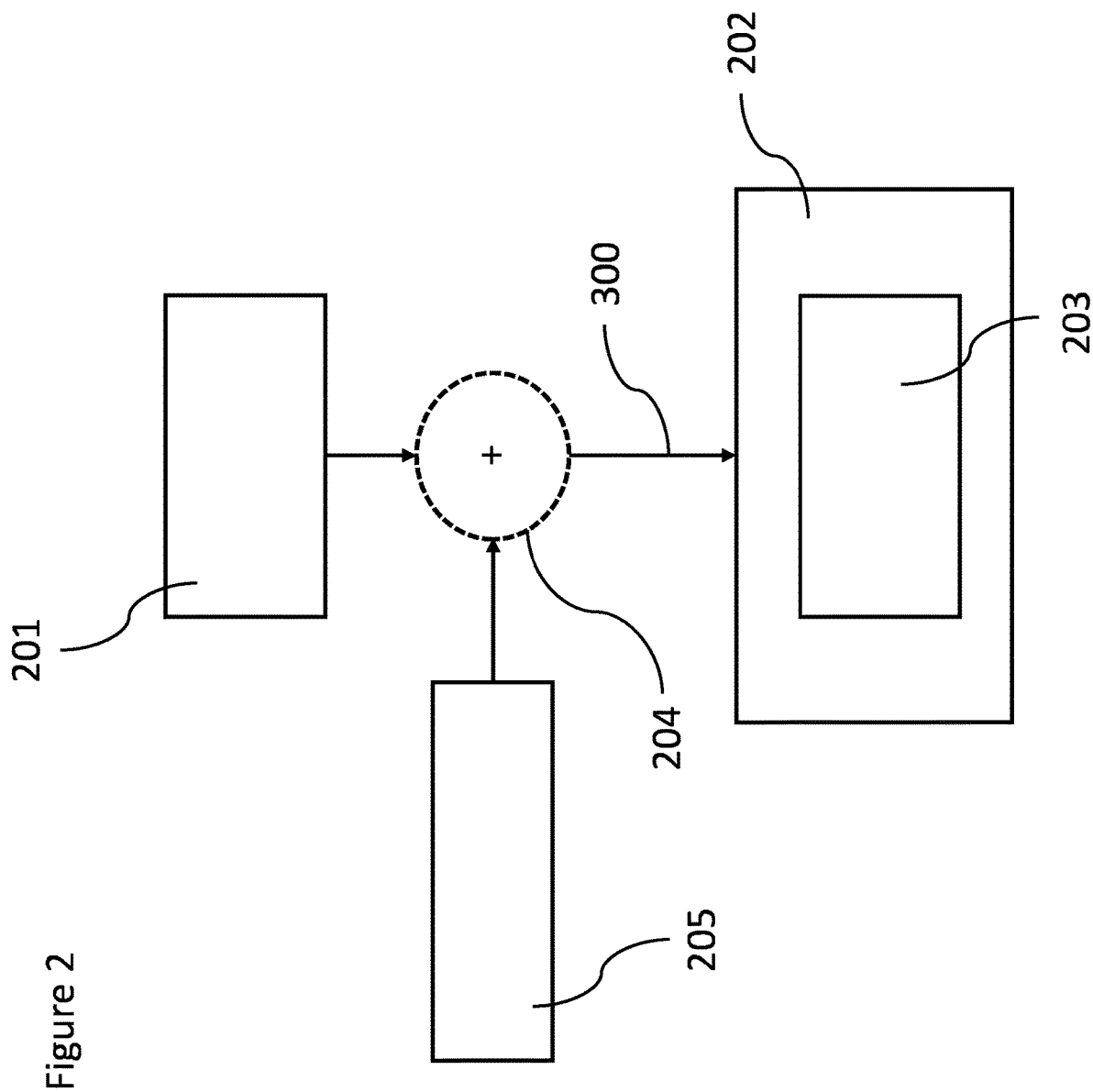
FIG. 2 schematically shows a block diagram of the transmission and reception of a body-coupled communication BCC system.

Reference is now made to FIG. 2 which shows schematically a BCC communication system 200. In some embodiments a transmitter 201, transmits a message packet 300, to a receiver 202, via the communication channel 103. In some embodiments the receiver 202 passes the received message packet 300 to a start of packet (SOP) detector 203. As the message packet 300 travels from the transmitter 201, to the receiver 202, via the communication channel 103, the message packet 300 may become noisy 204 due to potential BCC channel noise factors 205. Typically BCC channel noise is of two forms, continuous noise and burst noise. Continuous noise errors are spread apart randomly across the entire message packet. Burst noise errors affect contiguous bits.

Figure 3:
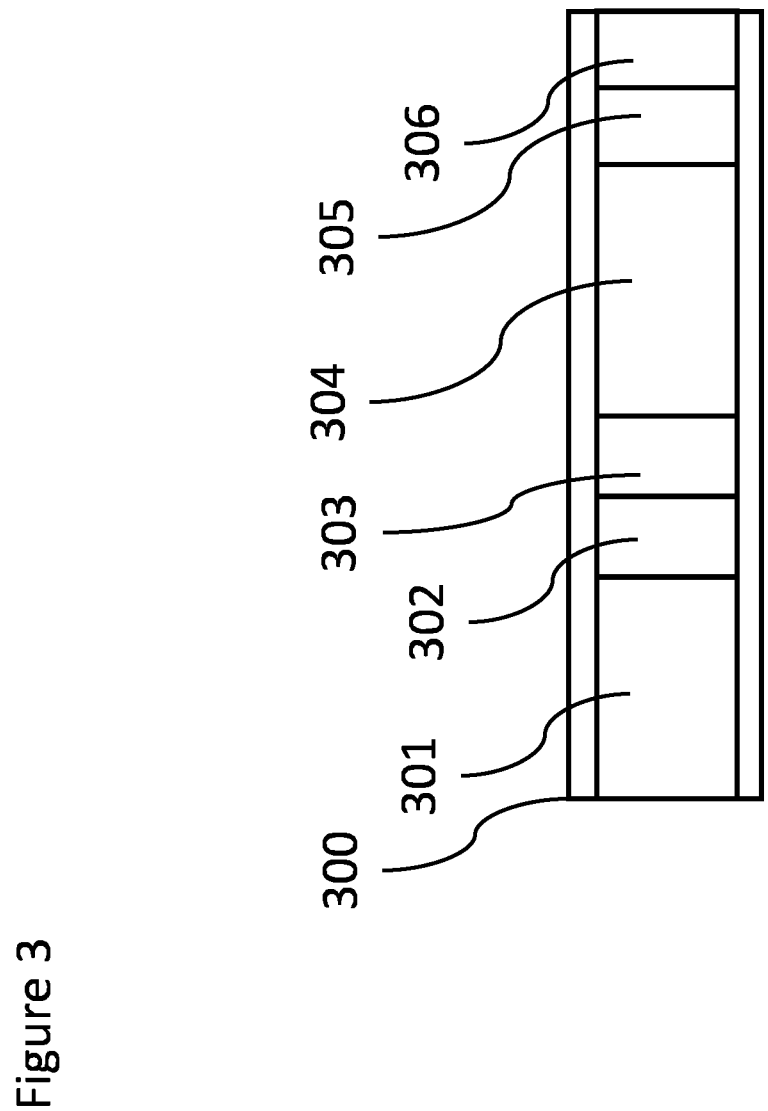
FIG. 3 schematically shows an embodiment of a data packet used in a body-coupled communication BCC system.

Reference is now made to FIG. 3 which shows an embodiment of a data packet 300, which may be transmitted from a transmitter 201 to a receiver 202. In some embodiments the data packet 300 may for example comprise: a preamble 301, a start of packet (SOP) indicator 302, a packet length indicator (PLI) 303, data bytes 304, a cyclic redundancy check 305, and an end of packet indicator (EOP) 306.

The packet length indicator (PLI) 303 provides information to the receiver 202 about the number of data bytes 304 present in the packet 300. A cyclic redundancy check (CRC) 305, may be utilized to detect errors in the message (data bytes) 304. The preamble 301 preceding the data bytes 304 may consist of a series of zeros. The preamble may last of the order of 100 μs duration. The preamble 301 may be used by an analogue front end (AFE) which will be described later for clock synchronization purposes. The start of a packet (SOP) 302 is used by the receiver 202 to identify the start of the data packet 300. If the SOP 302 is detected correctly it reduces the need for packet re-transmission. If the receiver cannot detect the start of the packet the whole packet is lost and re-transmission of the information is required to recover that information. If the number of re-transmissions is reduced this will improve the communication throughput (effective data rate). The effective data rate is a measure of the information that reached the receiver. The effective data rate takes into account all losses due to re-transmissions and lost packets.

It should be appreciated that other data packet formats may be used in other embodiments. One or more fields may be omitted. One or more additional fields may be provided. The order of the fields may be changed.

Some embodiments provide an integrated circuit body-coupled communication (BCC) transceiver.

One of the challenges for body-coupled communication (BCC) systems is the form of transceiver architecture that can achieve high robustness with a relative low power operation. This may be achieved by some embodiments.

Body coupled systems may advantageously have a low power consumption. Low power consumption for example tends to come with lower heat dissipation. This is advantageous if the device is being used against the skin of a user. Low power consumption is advantageous in applications where a device needs to be recharged or where there is a limited energy supply (for example kinetic or solar energy).

Embodiments may have application in any other suitable communication system. The communication system may or may not have a low power consumptions.

Some embodiments may be used where the distance between the transmitter and receiver is relatively large as compared to the available power.

The transceiver may in some embodiments be implemented by a single integrated circuit. In other embodiments, the transceiver may be integrated into a larger function or device. In some embodiments, one device may have a transmitter and another device may have a receiver. In some embodiments, a separate transmitter and receiver may be provided in a device.

The transceiver may achieve relatively high data rates (for example, 1 Mb/s).

The transceiver may be resilient to noise.

The start of packet detector may be economic in terms of area for the associated circuitry and/or required power. Power-usage of body-coupled communication devices may be a concern in some situations. This may be addressed by some embodiments.

Figure 4:
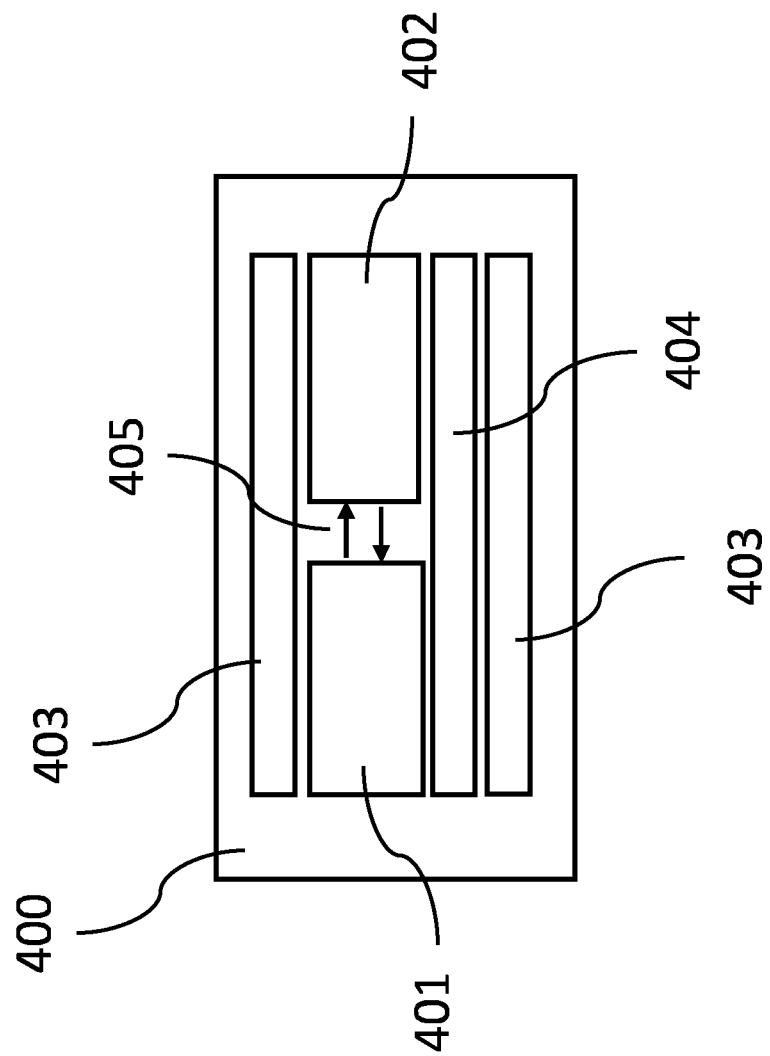
FIG. 4 schematically shows an embodiment of a body-coupled communication BCC system architecture.

Reference is now made to FIG. 4 which shows an embodiment of body-coupled communication (BCC) device architecture 400. In some embodiments the BCC device architecture 400 may comprise: a BCC transceiver integrated circuit 401, a host processor 402, electrodes 403, and a battery and power management module 404. The BCC transceiver integrated circuit 401 may communicate with the host processor 402 via a serial peripheral interface 405. The electrodes 403 are in contact with the body and may be used to transmit and receive signals. The battery and power management module 404, are connected to the BCC transceiver integrated circuit 401, and host processor 402.

In some embodiments the host processor 402 is part of a device that uses BCC capability to communicate with other BCC capable sensors/devices. The host processor 402 may configure the settings (initially) and pass on associated or other data to the BCC integrated circuit transceiver 401 which is to be transmitted to another BCC device. The BCC integrated circuit 401 is configured to packetize, and sending data. The BCC integrated circuit is configured to receive and extract data from a data packet. The host processor 402 may then read the extracted sensor data that is received by the BCC integrated circuit 401 via a serial peripheral interface (SPI) 405.

Figure 5:
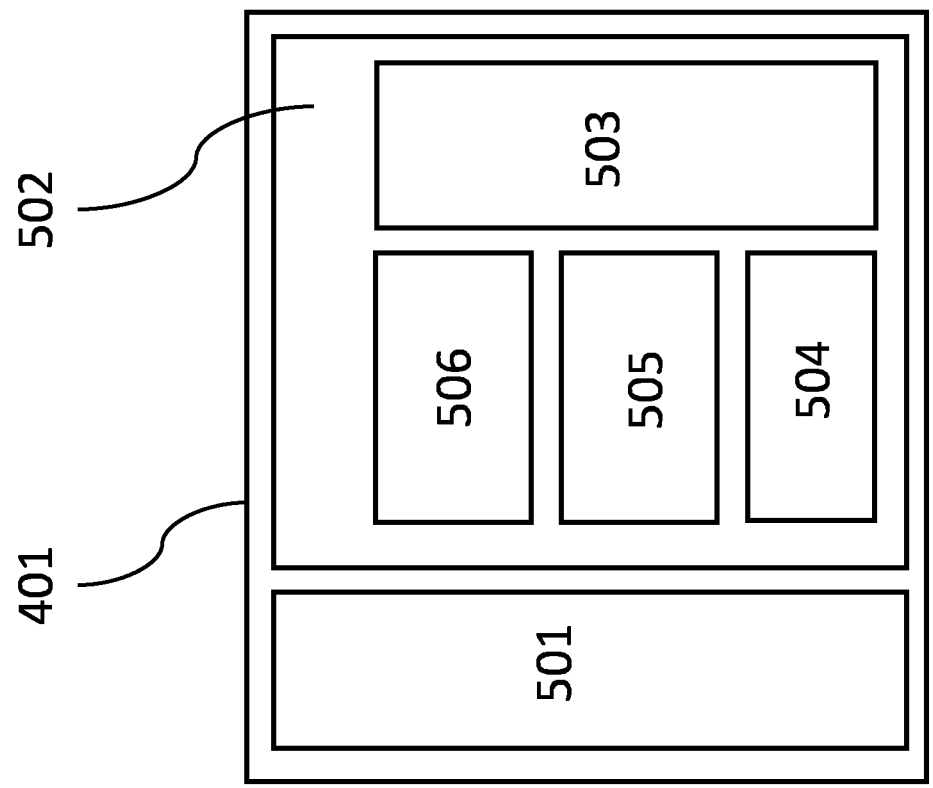
FIG. 5 schematically shows an embodiment of a body-coupled communication BCC integrated circuit IC system architecture.
Figure 6:
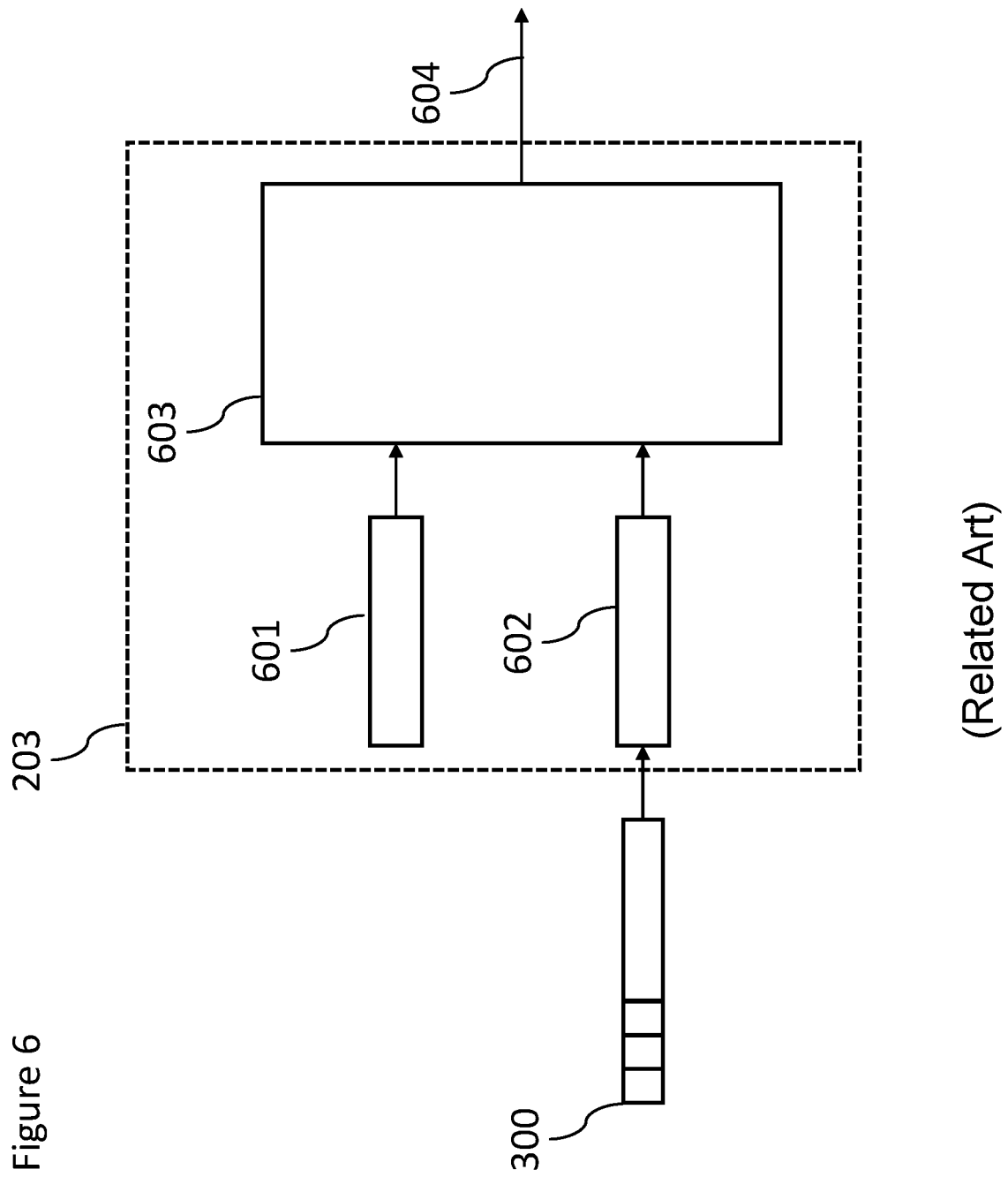
FIG. 6 which shows a known start of packet (SOP) detector.

Reference is now made to FIG. 5 which shows one embodiment of the body-coupled communication BCC transceiver integrated circuit 401. In some embodiments the BCC transceiver integrated circuit 401 may comprise an analog front end (AFE) 501 and a digital subsystem 502. The digital subsystem 502 may comprise: host interface control logic 503, system control logic 504, receive logic 505, and transmit logic 506. The AFE 501 may handle the interfacing and buffering to drive the electrodes 403, transmit integrated circuit-level encoding and decoding, local clock synchronization, input signal amplification, etc. The digital subsystem 502 may handle functions such as transmit and receive packet processing, system control, and host processor interfacing.

A BCC receiver should detect the start-of-packet (SOP) as accurately as possible. Typically the larger SOP the higher the accuracy of detection. Some embodiments may use a SOP which is 64/128-bits. However, this is by way of example and smaller or larger bit lengths may be used for the SOP. The SOP is preceded by 1000-bits of the preamble which may be used for synchronization purposes. The preamble can alternative be larger or smaller than this number of bits. For example, the preamble can be less than or more than 100 clock cycles. As a result of noise, the receivers may pick up corrupted message packets. A receiver must therefore be able to interpret the SOP packets accurately despite the presence of corrupted bits in the SOP packet. The number of corrupted bits that the SOP detector can tolerate and still interpret the SOP packets accurately is called the 'threshold' or 'noise tolerance level'. Having a threshold which can be set means that the system may be advantageously adapted from one use to another without the need for a major overhaul.

In embodiments, the threshold value to be utilized by a receiver may be dynamically set. The effective threshold may depend on the noise whilst the actual noise level in the system is not known a priori. Threshold levels not matching the actual noise (higher or lower) may reduce the accurate detections. Accordingly, some embodiments provide a start of packet detector that have a threshold value which can be set in dependence on the noise levels.

Figure 7:
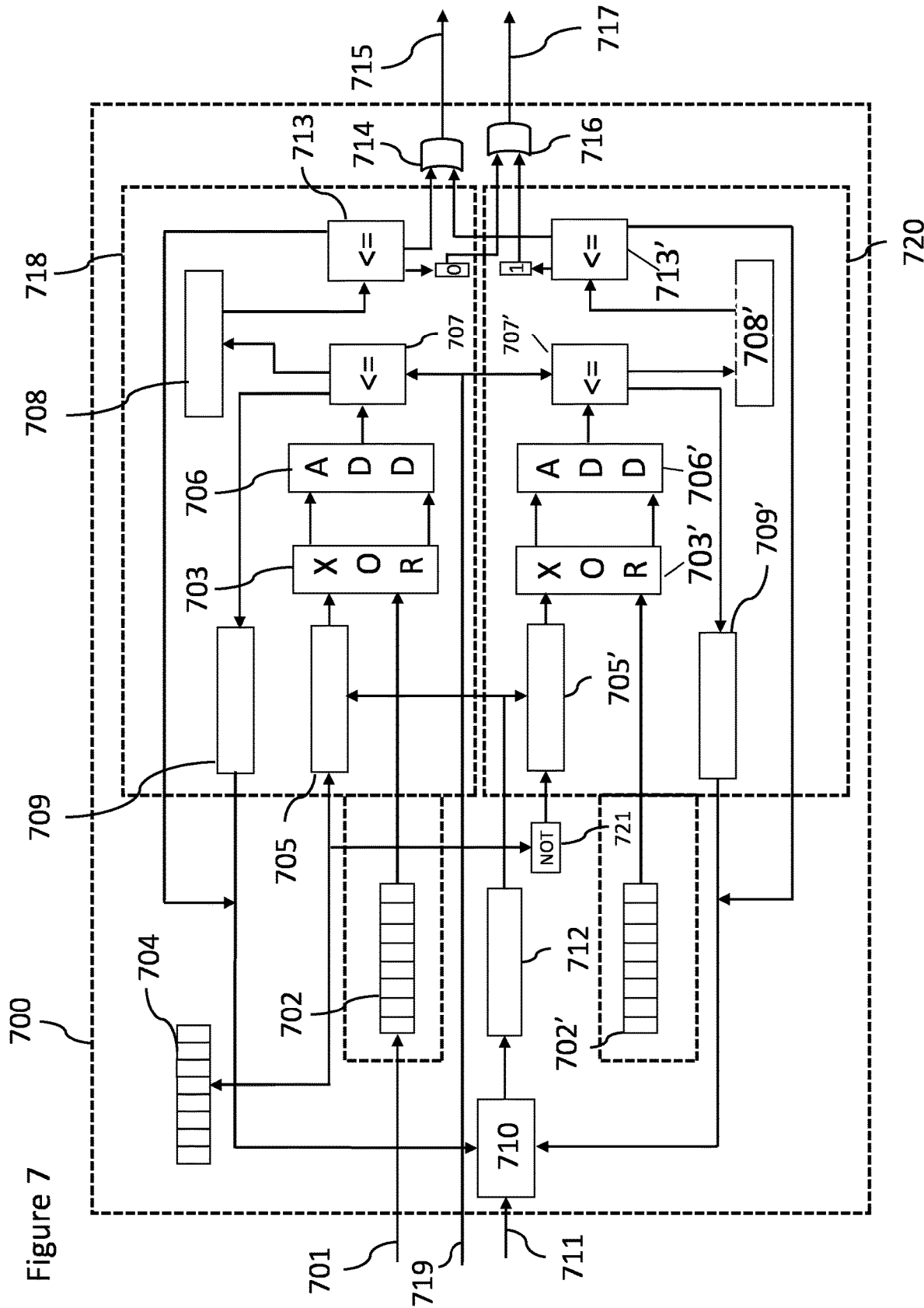
FIG. 7 schematically shows an embodiment of start of packet detector according to an embodiment.

Reference is now made to FIG. 7 which shows an embodiment of a start of packet detector. One or more of the blocks may be implemented in dedicated hardware. Alternatively or additionally one or more functions may be implemented by software. For example, general purpose hardware may use dedicated software to perform this function. Some embodiments may be implemented using both hardware and software. In the following example 8 bit registers etc. are used. It should be appreciated that 8 bits is by way of example only and other embodiments may be used with N-bit registers etc. where N is a suitable integer. The start of packet detector may have a normal polarity block 718 and an opposite polarity block 720.

FIG. 7 shows an input signal 701, which enters an 8-bit register 702. This is start of packet data which is received. The register 702 is inside the normal polarity block.

The normal polarity block 718 will be described first. The register 702 provides an output to an 8-bit XOR operator 703. Separately an 8-bit stored reference SOP code from a reference SOP store 704 (outside the normal polarity block) is provided to the 8-bit XOR operator 703. In some embodiments the length of the SOP is longer than 8 bits. In some embodiments the SOP may be m×N bit long. N is as discussed above and is an integer. In the example which is now described m is 8. However it should be appreciated that this is by way of example only.

It should be appreciated that some embodiments may be used where the number of bits of the SOP is not equal to m×N.

A counter may be provided to control which respective subset of reference start of packet information is used by the first stage. This may ensure that each subset of reference start of packet information is used in the correct order. It should be appreciated that in other embodiments, different logic may be used. A value of the counter may be changed if there is a match between a respective subset of received start of packet information with a respective subset of reference start of packet information. The counter may be incremented or decremented. In this way, when a give value of the counter is achieved, it can be determined that the whole of the SOP has been checked.

In this embodiment, a byte counter is provided. A byte counter function 705 defines the reference byte which is obtained from the reference SOP store. The byte counter may be provided outside of the normal polarity block. The byte counter function is represented by a number of the function blocks as will be discussed later. Function block 705 provides the current value of the byte counter. This controls which byte of the reference SOP bytes is retrieved from the reference SOP store for input to the XOR function 703. When the byte counter has, for example, the value 1, the first byte is retrieved from the SOP reference store.

It should be appreciated as the first byte is read out of the register 702, the next byte of the received SOP is read in. A clock counter function is provided. The clock counter function is represented by a number of the function blocks as will be discussed later. This clock counter will count up to 8 unless reset by the byte counter. This is described in more detail later.

The first stage may thus comprise an exclusive OR function configured to perform a respective exclusive OR function between said received start of packet information subset and the respective reference start of packet information subset. The exclusive OR function will advantageously provide one value when the reference and received value are the same and a different value when the reference and received value are different. The XOR operator effectively compares the reference SOP byte to the received byte of the SOP byte. The output of the 8-bit XOR operator 703 will generate a 1 where the inputs of the byte counter 705 is 0 and the input of the 8-bit register 702 is 1, and vice versa (indicating a mismatch between the received SOP value and the respective reference SOP value). If however inputs are both 0s, or if both inputs are 1s, (indicating a match between the received SOP value and the respective reference SOP value) the output of the 8-bit XOR operator 703 will generate a 0. The XOR operator 703 therefore compares the received SOP data with the reference SOP to determine if there is a match. A matched bit will provide a 0 value output.

The first stage may comprise an adder function configured to add the output of said exclusive OR function and to provide a summed output to a first comparator, said first comparator configured to compare said summed output to a threshold. Advantageously, by summing the output of the exclusive OR function, a value is obtained which will be indicative of the degree of match between the reference and received start of packet information. By comparing this value to a threshold, it can be simply determined if the respective subsets of information are considered to be a match or not.

In one embodiment, the 8-bit output of the XOR operator 703 is then passed to an 8-bit ADD operator 706. This ADD operator will sum the eight values output from the XOR operator. The 8-bit ADD operator 706 provides the sum to a comparator 707 which compares the received sum to first threshold value, set by a threshold input 719.

The first stage may be thus be configured to use a threshold to determine if there is a match, the threshold be configurable for each subset. This allows for the threshold to be varied, for example in response to noise level.

In some embodiments, the threshold input can be changed on a per byte basis. In other embodiments, the threshold input can be varied on a per SOP basis. In other embodiments, the threshold may be controlled. In some embodiments, the threshold value may not be variable. The threshold value will determine the amount of noise that can be tolerated and still provide a match, in some embodiments.

The start of packet detector may comprise a second comparator for determining if all the subsets of said start of packet have been determined for a match and if so to cause a start of packet detected output to be output by said output.

If the sum from the ADD operator 706 is less than or equal to the threshold value, an output is provided which increases the value of the byte counter by a value of 1, as represented by function block 708. This may be by the assertion of a signal or in any other suitable way and may be via the second comparator. The output causes the second comparator 713 to compare the updated byte counter to the value of m (8 in this example) to determine if all of the bytes of the SOP have been compared to respective reference SOP. If not the output of the second comparator will cause the byte counter to increment by 1. In other words, the byte counter will be incremented providing there is deemed to be a match between the reference and received SOPs and the number of bytes which have been compared is less than the maximum amount.

If the sum is greater than equal to the threshold, the output of the first comparator 707, represented by function 709, does not increment the byte counter. This output is provided to a clock counter function 710 which will increment the clock count by one, as represented by function block 712. This is described in more detail later. It should be appreciated that in other embodiments, the counter may instead be decremented.

The first stage may be configured to cause a start of packet detected output to be output by said output if all the subsets of the start of packet information have been determined to match. This may be simple to implement in that if any respective subsets do not match, the n it is considered that there is not match.

The start of packet detector may comprise a second stage arranged in parallel with said first stage, the second stage configured to compare said respective subset of received start of packet information with an inverse of the respective subset of reference start of packet information. This is useful with devices which do have a common electrical ground. The detector may therefore interpret the received message as being the opposite polarity (i.e. the binary 1's may be interpreted as 0's and vice versa). Accordingly, by having the second stage, the SOP detector is able to consider both possible polarities.

BCC receivers and transmitters typically do not have a common electrical ground, as such no reference voltage may exist. The receiver may therefore interpret the received message as being the opposite polarity (i.e. the binary 1's may be interpreted as 0's and vice versa). Accordingly, the SOP detector should consider both possible polarities as there may be no certainty as to which polarity is being received. As mentioned previously there is a normal polarity block 718 and an opposite polarity block.

A NOT function 721 is provided to inverse the values of the reference SOP and output the inverted reference SOP values to the XOR operator 703' in the opposite polarity block.

The opposite polarity block has the same functions and blocks as the normal polarity block but those functions and blocks are referenced with the same reference number and a ' as a suffix, e.g. 703'.

The output of the second comparator of the normal polarity block is provided as the input to a first OR gate 714. The output of the second comparator of the opposite polarity block is provided as a second input to a first OR gate. When either of the outputs of the second comparators indicates that the all the bytes of the SOP have been compared, the output of the OR gate will be high to provide a synchronization output 715. This indicates that the SOP of the received data has been received.

The output may be configured to output information indicating if said start of packet detected output is dependent on said determining of said first stage or said second stage. In some embodiments, this may be used for understanding the content of the packet. This allows the circuitry to understand what represents a logic 1 and what represents a logic 0 in the data.

A second OR gate 716 is also provided. The output of this OR gate is used, when a synchronization output is provided by the first OR gate, to determine whether the SOP was matched by the normal polarity SOP block or the opposite polarity SOP block. According, when second comparator 713 of the normal polarity blocks determines that all bytes have been compared, the second comparator 713 of the normal polarity block will output a 0 to the second OR gate 717. When second comparator 713' of the opposite polarity blocks determines that all SOP bytes have been compared, the second comparator 713' of the opposite polarity block will output a 1 to the second OR gate 717. Thus the output of the second OR gate provides polarity information 717.

The value is then passed to the byte counter block 705 in the normal polarity block 718, and the byte counter block 705' in the opposite polarity block 720. If the value was passed to the function block 708, and the byte counter 705 was increased by a value of 1, the value is then passed to a second threshold operator 713, wherein if the value is less or equal to than the value of the second threshold operator 713, the value is passed to an OR operator 714, and finally forms the normal output 715. If however, the value is less than or equal to the value of the second threshold operator 713, the value is passed to an OR operator 716, and finally forms the opposite polarity output 717. These steps are undertaken in a normal polarity block 718. An opposite polarity block 720 is also present and comprises an identical set of steps as disclosed above but for bits that are of the opposite polarity.

In some embodiments a received SOP packet 300 is divided into 8-bit segments. 8 bytes must be successively detected in the received bits for a successful SOP detection. For example, the two 8-bit registers 702, and 702' may be initialized by setting each bit in the normal polarity block 718 register 702 to a zero (0x00) and by setting each bit in the opposite polarity block 720 register 702' to a one (0xFF). The opposite polarity block 720 register 702' may be initialized by setting each bit to one, as the pre-SOP code (e.g. the preamble) of the opposite polarity block 720 starts with eight zeros and so initializing the register by setting each bit to zero may cause an erroneous match for the first byte. The shift register for the opposite polarity block may be required when the remaining number of preamble bits is less than eight to prevent an erroneous first byte match. For a greater number of bits, both the shift registers may have equal values such that only one would be sufficient.

In some embodiments a received bit is shifted into the 8-bit registers 702, and 702' for every clock cycle. A clock counter is used to count the stage number for which the current comparison should take place starting from an initial value of zero indicating the first stage. Each stage saves its own history of successful 8-bit matches in the byte counter which is initialized to zero to indicate the first byte of the SOP.

For example, in the normal polarity block 718 for the first clock cycle, the initial value (zero) of the clock counter indicates the first stage of the algorithm. The first received bit 701 will be shifted to the first (least significant bit) position of the 8-bit register 702 (register 702' in the opposite polarity block 720) while the other bits are shifted up by one position (towards the most significant bit position). The 8-bits of the register 702 are then compared to the bth segment of SOP, where the value of b is indicated by the byte counter. As the initial value indicates the first byte, the first reference SOP byte is used for comparison. If the comparison produces errors which are lower than the threshold limit then byte counter is incremented or else reset.

In the second clock cycle, the next received bit is shifted into the register 702 (register 702' in the opposite polarity block 720) and the clock counter is incremented by 1. Now the second stage of the algorithm executes by comparing its byte counter value (which is again initially zero) and updates the byte counter accordingly. This continues for all the eight stages. After the eight clock cycles, the clock counter 712 is reset to zero such that the first stage executes again. However this time, the 8-bits of the register 702 (register 702' in the opposite polarity block 720) is compared with the second byte of the reference SOP (if the previous byte was a match) and the byte counter gets updated accordingly. This process repeats until all 8 bytes or segments of the SOP are successively detected and then the synchronization signal 715 is set to a high state. A similar operation follows in the opposite polarity block 720, with the difference that the SOP segment retrieved is inverted (NOT 721) before comparison. Based on the block where the SOP was detected, polarity information is generated.

Some embodiments may be used with relatively long SOPs, for example 64 bits or 128 bit. This is by way of example only and in different embodiments, different lengths of SOPs may be used.

The implementation of the SOP may define the quality of the communication link, which depends on one or more aspects such as used protocol, bit rates, data throughput, re-transmits, noise levels etc.

In the present embodiment an 8-stage, 8-bit correlator is shown, it should be appreciated that N-stages could be used with n-bits. For example, the present embodiment utilizes an 8-stage, 8-bit semi-parallel detection approach for a 64-bit SOP. For example, another embodiment may utilize a 16-stage, 16-bit semi-parallel detection approach for a 128-bit SOP. Further, it should be appreciated that various numbers of stages (N-stages) could be used with various numbers of bits (n-bits).

In some embodiments the noise tolerance level (threshold) may be applied per byte. Some embodiments may allow a re-utilization of low cost 8-bit XOR and ADD units irrespective of the SOP packet length. This may lead to a reduced (for example a factor 2) physical area and power consumption. Having noise thresholds per byte in some embodiments may allow for a fixed optimal threshold level which may provide a high percentage of accurate detections across a larger variation in the noise levels.

In some embodiments, the threshold per byte condition may be relaxed. It may be that say only one of the compared bytes can exceed the threshold limit. The number bytes which can exceed the threshold limit is a design choice. In some embodiments, this may be dependent on the number of bytes in the SOP. In some embodiments the applicable threshold may be say one more than the primary byte threshold. For example if the primary threshold is 3 per byte, then the failed byte would have to meet a threshold of 4. If the SOP is say 8 bytes, this allows one of the bytes to fail to meet the threshold and for their still to be a SOP detected. It should be appreciated that the values given are by way of example only and may be different in different embodiments. The threshold implementation may use logic that gives a flag when more than a given number of bits per byte gets corrupted. Then the whole byte is considered corrupted. The threshold logic decides how many corrupted bytes will be accepted before the whole packet is discarded.

In the described embodiments, examples of types of logic functions, for example XOR and OR. These are by way of example only and different embodiments may have different logic functions.

In the described embodiments, the values of 1 and 0 indicate particular conditions. For example, a "1" indicates synchronization. However, it should be appreciated that this is by way of example and in other embodiments the other of "0" and "1" may be used.

In the described embodiments, an adder function has been used but this is by way of example only. In different embodiments, a different function may be used.

In alternative embodiments, the start of packet detector may be provided any suitable digital communication systems which use SOP detectors such as those in compliance with the IEEE standards: IEEE802.11b/g/n (WIFI) and IEEE802.15 (Bluetooth). Other embodiments may be used with IEEE 802.15.4 or other suitable low rate wireless personal area networks.

It should be appreciated that some embodiments use SOP detection in the digital domain.

It should be appreciated that in some embodiments the threshold may be simply specified by a user without the need for complex automatic threshold adjustment logic.

Some embodiments may use a simple direct correlation based approach to detect a SOP which is not encoded nor spread using a spreading function.

In one modification, a value is stored for each comparison between a part of the received SOP and reference SOP. The value will one value if there is a match and a different value if not. When all of the SOP has been compared to the reference SOP, the values are used to determine if there whole SOP is considered to match the reference value. This may require the value for each comparison to have the one value. In other embodiments, there may be a threshold number of values which are required to have the one value.

In another modification, the value for each comparison is accumulated with the previous comparison value(s). The accumulated value may be compared with a threshold value to determine if there is a match.

It should be appreciated that the above described arrangements may be implemented at least partially by an integrated circuit, a chip set, one or more dies packaged together or in different packages, discrete circuitry or any combination of these options.

Figure 8:
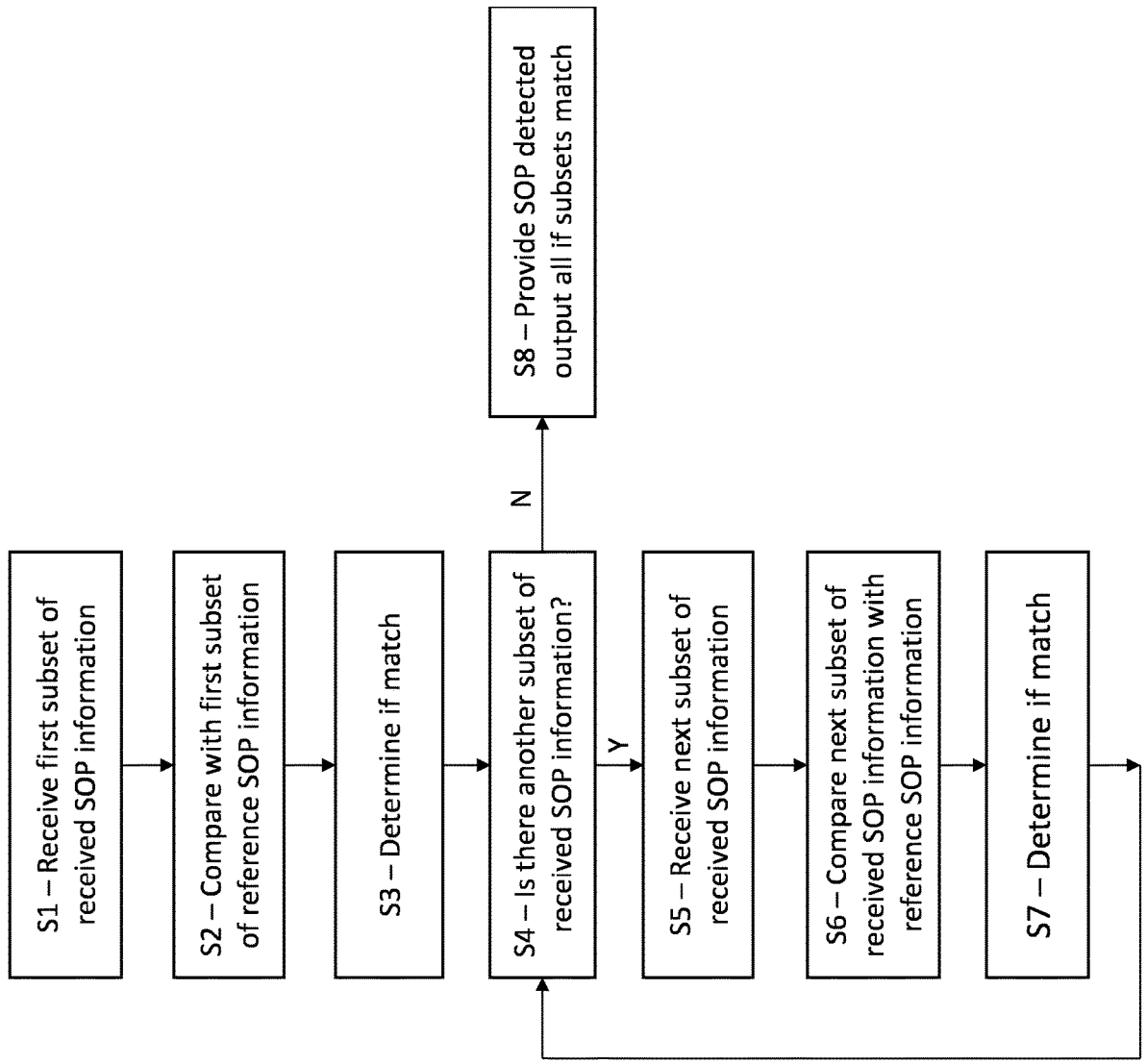
FIG. 8 shows a method of an embodiment.

Reference is made to FIG. 8 which shows a method of some embodiments. In step S1, a first subset of received start of packet information is received.

In step S2, the received first subset of received SOP information is compared with a respective first subset of reference SOP information.

In step S3, it is determined if there is a match between the first subset of reference SOP information and the corresponding first subset of received SOP information. The information as to whether or not there is a match may be stored, in some embodiments.

In step S4, it is determined if there is another subset of received SOP information. If so, the next step is step S5.

In step S5, the next subset of received SOP information is received.

In step S6, the next subset of received SOP information is compared with the respective subset of reference SOP information.

In step S7, it is determined if there is a match between the respective reference SOP subset of information and received SOP subset of information. The method then loops back to step S4.

If it is determined in step S4 that there are no more subsets of received SOP information, the next step is step S8. In step S8, a detected SOP output is provided if all of the comparisons match. Thus, if all of the subsets of the SOP information which have been received match with the respective reference SOP information, then an output is provided indicating that an SOP has been detected.

It should be appreciated that when determining whether or not there is a match (steps S3 and S7), a respective threshold may be provided. This may be as previously described.

Various embodiments with different variations have been described here above. It should be noted that those skilled in the art may combine various elements of these various embodiments and variations.

Such alterations, modifications, and improvements are intended to be part of this disclosure, and are intended to be within the scope of the present invention. Accordingly, the foregoing description is by way of example only and is not intended to be limiting. The present invention is limited only as defined in the following claims and the equivalents thereto.

The invention claimed is:

1. A start of packet detector, comprising:
an input, the input configured to receive input data, wherein the input data comprises start of packet information;
a first stage, the first stage configured to determine if there is a match between a subset of received start of packet information with a respective subset of reference start of packet information,
wherein the first stage is configured to repeat said determining for each of said subsets of received start of packet information and said respective subset of reference start of packet information,
wherein a value of a counter is changed if there is a match between one of said subsets of received start of packet information with said respective subset of reference start of packet information;
a second stage, the second stage arranged in parallel with said first stage,
wherein the second stage is configured to compare said subset of received start of packet information with an inverse of the respective subset of reference start of packet information; and
an output, the output configured to provide a start of packet detected output,
wherein said start of packet detected output is dependent on a comparison of a value of said counter with a threshold,
wherein said start of packet detected output is dependent on said determining of said first stage or said second stage.

2. The start of packet detector as claimed in claim 1, wherein the counter is configured to control which respective subset of reference start of packet information is used by said first stage.

3. The start of packet detector as claimed in claim 1, wherein said threshold is configurable for each subset.

4. The start of packet detector as claimed claim 1, wherein said first stage comprises an exclusive OR function configured to perform a respective exclusive OR function between said received start of packet information subset and the respective reference start of packet information subset.

5. The start of packet detector as claimed in claim 4, wherein said first stage comprises an adder function configured to add the output of said exclusive OR function and to provide a summed output to a first comparator, said first comparator configured to compare said summed output to the threshold.

6. The start of packet detector as claimed in claim 1, wherein said first stage is configured to cause a start of packet detected output to be output by said output if all the subsets of said start of packet information have been determined to match.

7. The start of packet detector as claimed in claim 6, comprising a second comparator for determining if all the subsets of said start of packet have been determined to match and, if so, to cause a start of packet detected output to be output by said output.

8. The start of packet detector as claimed in claim 1, wherein said output is configured to output information indicating if said start of packet detected output is dependent on said determining of said first stage or said second stage.

9. A body coupled device comprising a start of packet detector, the start of packet detector comprising:
an input, the input configured to receive input data, wherein the input data comprises start of packet information;
a first stage, the first stage configured to determine if there is a match between a subset of received start of packet information with a respective subset of reference start of packet information,
wherein the first stage is configured to repeat said determining for each of said subsets of received start of packet information and said respective subset of reference start of packet information,
wherein a value of a counter is changed if there is a match between one of said subsets of received start of packet information with said respective subset of reference start of packet information;
a second stage, the second stage arranged in parallel with said first stage,
wherein the second stage is configured to compare said subset of received start of packet information with an inverse of the respective subset of reference start of packet information, and
an output, the output configured to provide a start of packet detected output,
wherein said start of packet detected output is dependent on a comparison of a value of said counter with a threshold,
wherein said start of packet detected output is dependent on said determining of said first stage or said second stage.

10. A method of detecting a start of packet, comprising:
receiving a first subset of received start of packet information;
comparing the first subset of received start of packet information with a respective first subset of reference to determine if there is a first match;
comparing the first subset of the received start of packet information with an inverse of the respective first subset of reference to determine if there is a second match;
changing a value of a count if the first match or the second match is determined;
repeating said receiving and comparing for subsequent subsets of received start of packet information and respective subsequent subsets of reference start of packet information; and
providing a start of packet detected output dependent on comparing the value of said count with a threshold.

11. The method as claimed in claim 10, wherein said comparing comprises using a first threshold with said first subset of received start of packet information and a second threshold with at least one other subset of received start of packet information.

12. The method as claimed in claim 10, comprising providing a start of packet detected output if all the subsets of said start of packet information have been determined to match.

* * * * *